United States Patent [19]
Cossart et al.

[11] Patent Number: 5,523,205
[45] Date of Patent: Jun. 4, 1996

[54] DNA PROBES SPECIFIC FOR HEMOLYTIC LISTERIA

[75] Inventors: Pascale Cossart; Jérôme Mengaud, both of Paris; Marléne Bohnert, Saint-Brieux, all of France

[73] Assignee: Institut Pasteur, Paris, France

[21] Appl. No.: 130,512

[22] Filed: Oct. 1, 1993

Related U.S. Application Data

[63] Continuation of Ser. No. 829,277, Feb. 3, 1992, abandoned, which is a continuation-in-part of Ser. No. 227,402, Aug. 2, 1988, abandoned.

[51] Int. Cl.$^6$ .............................. C12Q 1/68; C12P 19/34; C07H 21/04
[52] U.S. Cl. .................... 435/6; 435/91.2; 536/24.32
[58] Field of Search .................. 435/6, 91.2; 536/24.32

[56] References Cited

U.S. PATENT DOCUMENTS

| | | | |
|---|---|---|---|
| 4,683,202 | 7/1987 | Mullis | 435/6 |
| 5,389,513 | 2/1995 | Baquero et al. | 435/6 |

OTHER PUBLICATIONS

Vicente et al., Ann. Inst. Pasteur/Microbiol., 138(7):250–251 (1987).
Mengaud et al., Inf. and Immun., 55(12):3225–3227 (1987).
Datta et al., App. and Enviro. Microbiol., 53(9):2256–2259 (1987).
Mengaud et al., Inf. and Immun., 56(4):766–772 (1988).
Datta et al., J. Assoc. Anal. Chem., 71(3):673–675 (1988).
Gaillard et al., Inf. and Immun., 52(1):50–55 (1986).
Cossart et al., Infection, 16 (Suppl. 2):S 157–S 159 (1988).
Kathariou et al., J. Bacteriol, 169(3):1291–1297 (1987).
Kathariou et al., Inf. and Immun., 56(2):534–536 (1988).
Rocourt et al., Int. J. Syst. Bacteriol., 37(3):298–300 (1987).
Vincente et al., FEMS Microbiol. Lett., 30:77–79 (1985).
Vicente et al., Ann. Inst. Pasteur/Microbiol., 138(3):385–387 (1987).
Kathariou et al., Ann. Inst. Pasteur/Microbiol., 183(2):256–258 (1987).
Hames et al., Nucleic Acid Hybridization, IRL Press, pp. 17–111 (1985).
Suggs et al., Proc. Nat'l. Acad. Sci. (USA), 78(11):6613–6617 (1981).
Domann et al., Nucleic Acids Research, IRL Press, 17(15):6406 (1989).

*Primary Examiner*—George C. Elliott
*Attorney, Agent, or Firm*—Finnegan, Henderson, Farabow, Garrett & Dunner

[57] ABSTRACT

DNA probes are capable of hybridizing to a portion of the genome of pathogenic *Listeria monocytogenes*, but do not hybridize to genomes of other Listeria species and other hemolytic bacteria. These probes are useful to identify food sources infected with *Listeria monocytogenes* and to distinguish these food sources from those infected with non-pathogenic Listeria species. In addition, methods for the detection of pathogenic Listeria in samples using the disclosed probes are provided. A method of detection using PCR amplification with primers specific for *L. monocytogenes* DNA is also disclosed.

11 Claims, 7 Drawing Sheets

```
FIRST nt.          10         20         30         40         50         60         70         80         90        100
   +1   GGATCCGATA ATCAAAACTA TCGTTGCTGT TTTGCTCGTC TTTTAAACGC ATAATAATGG ATTTTTCTTT AAAAATTGAG TAATCGTTTC
        CCTAGGCTAT TAGTTTTGAT AGCAACGACA AAACGAGCAG AAAATTTGCG TATTATTACC TAAAAAGAAA TTTTTAACTC ATTAGCAAAG
 +101   TAATACACCT GAAAGTGATG CATTTAAAAA AATTGGCCCA TGGTAAATGT TGAGATTGTC TTTCTTTTGG ACCGTATTCC TGCTTCTAGT
        ATTATGTGGA CTTTCACTAC GTAAATTTTT TTAACCGGGT ACCATTTACA ACTCTAACAG AAAGAAAGAA TGGCATAAGG ACGAAGATCA
 +201   TGTTGGTACA ATGACATCGT TTGTGTTTGA GCTAGTGGTT TGGTTAATGT CCATGTATG TTTTGCTCTA ATATCGATGT ATCATGTGTA
        ACACCATGT TACTGTAGCA AACACAAACT CGATCACCAA ACCAATTACA GGTACAATAC AAAACGAGAT TATAGCTACA TAGTACACAT
 +301   AGAGCGCTGC TAGGTTTGTT GTGTCAGGTA GAGCGGACAT CCATTGTTTT GTAGTTACAG AGTTCTTTAT AGCTCATCGT CAGTTATTAA
        TCTCGCGACG ATCCAAACAA CACAGTCCAT CTCGCCTGTA GGTAACAAAA CATCAATGTC TCAAGAATAA TCGAGTAGCA GTCAATAATT
 +401   TTTTCCGCCT AATGGGAAAG TAAAAAAGTA TAAAATAAAA CAGAGTAATA AACTAATGT TGGCTTATTC ACAAAATGGC CCCCTCCTTT
        AAAAGGCGGA TTACCCTTTC ATTTTTTCAT ATTTTATTTT GTCTCATTAT TTGATTACA ACCGAATAAG TGTTTTACCG GGGGAGGAAA
 +501   GATTAGTATA TTCCTATCTT AAAGTGACTT TTATGTTGAG GCATTAACAT TTGTTAACGA ACAGCAGGAC TAGAATAAAG CTATAAGCA
        CTAATCATAT AGGATAGAA TTTCACTGAA AATACAACTC CGTAATTGTA AACAATTGCT TGTCGTCCTG ATCTTATTTC GATATTTCGT
 +601   AGCATATAAT ATTGCGTTTC ATCTTTAGAA GCGAATTTCG CCAATATTAT AATTATCAAA AGAGAGGGGT GGCAAACGGT ATTTGGCATT
        TCGTATATTA TAACGCAAAG TAGAAATCTT CGCTTAAAGC GGTTATAATA TTAATAGTTT TCTCTCCCCA CCGTTTGCCA TAAACCGTAA
 +701   AAAATGTAGA AGGAGAGTGA AACCCCATGA AGAAAATTCA CTAGTTTTA AATCATCTCCG CTGCAAGTC CTGCAAGTC ACGGAGATGC
        TTTTACATCT TCCTCTCACT TTGGGTACTT TCTTTTAAGT GATCAAAAAT TCGTAGAGGC GGACGTTCAG TGCCTCTACG
 +801   GATGCATCTG CATTCAATAA AGAAAATTCA ATTTCATCCA TGGCACCACC AGCATCTCCG CCTGCAAGTC ACGGAGATGC CTAAGACGCC
        CTACGTAGAC GTAAGTTATT TCTTTTAAGT TAAAGTAGGT ACCGTGGTGG TCGTAGAGGC GGACGTTCAG TGCCTCTACG GATTCTGCGG
 +901   ATGAAATCGA TAAGTATATA CAAGGATTGG AACACAATGTA TTAGTATACC ACGGAGATGC AGTGACATGC GTGCCGCCAA AAACACGCGG
        TACTTAGCT ATTCATAT GTTCCTAACC TTGTTACAT AATCATATGG TGCCTCTACG TCACTGTTTA CACGGCGGTT TTTGTGCGCC
+1001   CAAAGATGGA AATGAATATA TTGTTGTGGA GAAAAGAAG AAATCCATCA ATCAAAATAA CAAGTTGTGA CAAGTTGTGA GAGCCTAACC
        GTTTCTACCT TTACTTATAT AACAACACCT CTTTTCTTC TTTAGGTAGT TAGTTTTATT GTTCAACACT GTTCAACACT CTCGGATTGG
```

FIG. 2A

```
+1101  TATCCAGGTG CTCTCGTAAA AGCGAATTCG GAATTAGTAG AAAATCAACC AGATGTCTC CCTGTAAAAC GTGATTCATT AACACTCAGC ATTGATTTGC
       ATAGGTCCAC GAGAGCATTT TCGCTTAAGC CTTAATCATC TTTTAGTTGG TCTACAGAG GGACATTTTG CACTAAGTAA TTGTGAGTCG TAACTAAACG

+1201  CAGGTATGAC TAATCAAGAC AATAAATCG TTGTAAAAAA TGCCACTAAA TCAAACGTTA ACAACGCAGT AAATACATTA GTGAAAGAT GGAATGAAAA
       GTCCATACTG ATTAGTTCTG TTATTTTAGC AACATTTTTT ACGGTGATTT AGTTTGCAAT TGTTGCGTCA TTTATGTAAT CACCTTTCTA CCTTACTTTT

+1301  ATATGCTCAA GCTTATCCAA ATGTAAGTGC AAAAATTGAT TATGATGACG AATGGCTTA CAGTGAATCA GAAGAAGTCA CAATTAATTG CGAAATTTGG TACAGCATTT
       TATACGAGTT CGAATAGGTT TACATTCACG TTTTTAACTA ATACTACTGC TTACCGAAT GTCACTTAGT CTTCTTCAGT GTTAATTAAC GCTTTAAACC ATGTCGTAAA

+1401  AAAGCTGTAA ATAATAGCTT GAATGTAAAC TTCGGCGCAA TTTTCGGCAA GAAAATGCAA TCAGTGAAGG GAAGAAGTCA TTAGTTTAA ACAAATTTAC TATAACGTGA
       TTTCGACATT TATTATCGAA CTTACATTTG AAGCCGCGTT AAAAGCCGTT CTTTTACGTT CTTCTTCAGT AATCAAATT TGTTTAAATG ATATTGCACT

+1501  ATGTTAATGA ACCTACAAGA CCTTCCAGAT TTTTCGGCAA AGCTGTTACT AAAGAGCAGT TGCAAGGCT TGGAGTGAAT GCAGAAAATC CTCCTGCATA
       TACAATTACT TGGATGTTCT GGAAGGTCTA AAAAGCCGTT TCGACAATGA TTTCTCGTCA ACGTTCGGCA ACCTCACTTA CGTCTTTTAG GAGGACGTAT

+1601  TATCTCAAGT GTGGCGTATG GCCGTCAAGT GCCGTCAAGT AGCTGTTACT ATTCCCATAG TACTAAAGTA ATGATTTCAT AAAGCTGCTT TTGATGCTGC CGTAAGCGGA
       ATAGAGTTCA CACCGCATAC CGGCAGTTCA CGGCAGTTCA TCGACAATGA TAAGGGTATC ATGATTTCAT TTCGACGAA AACTACTTA GCATTCGCCT

+1701  AAATCTGTCT CAGGTGATGT AGAACTAACA AATATCATCA AAAATTCTTC CTTCAAAGCC GTAATTACG ATTTAAATGC AAAAGATGAA GTTCAAATCA
       TTTAGACAGA GTCCACTACA TCTTGATTGT TTATAGTAGT TTTTAAGAAG GAAGTTTCGG CATTAAATGC TATTTACTT CAAGTTAGT

+1801  TCGACGGCAA CCTCGGAGAC TTACGCGATA AAAATTGTCC TATATTGAAG AGGCGCTACT TTTAATGAGC AAACACCAGG AGTTCCCATT CAAACTTCCT
       AGCTGCCGTT GGAGCCTCTG AATGCGCTAT TTTAAGCAGG TCCGCGATGA AATTAGCTC TTTGTGGTCC TCAAGGGTAA GTTTGAAGGA

+1901  AAAAGACAAT GAATTAGCTG TTATTAAAAA CAACTCAGAA TATATAAAAA CAACTTCAAA AGCTTATACA GATGGAAAAA TTAACATGA TCACTCTGA
       TTTTCTGTTA CTTAATCGAC AATAATTTTT GTTGAGTCTT ATATATTGT GTTGAAGTTT TCGAATATGT CTACCTTTTT AGTGAGACCT

+2001  GGATACGTTG CTCAATTCAA CATTTCTTGG GATGAAGTAA ATTTGCCAGG TGAAGGTAAC GAAATTGTTC AACATAAAAA CTGGAGCGAA AACAATAAAA
       CCTATGCAAC GAGTTAAGTT GTAAAGAACC CTACTTCATT TAAACGGTCC ACTTCCATTG CTTTAACAAG GACCTCGCTT TTGTATTTTT

+2101  GCAAGCTAGC TCATTTCACA TGTCCATCT ATTTGCCAGG TAACGCGAGA ATATTAATTAC TTACGCTAA AATGCGATT AGAATGCACT GGTTTAGCTT
       CGTTCGATCG AGTAAAGTGT ACAGGTAGA TAAACGGTCC ATTGCGCTCT TATATTAATTAC ATTGCGATT TCTTACGTGA CCAATCGAA

+2201  GAGAACGGTA ATTGATGACC GGAACTTACC ACTTGTGAAA AATAGAAATA TCTCCATCTG GGGCACCACG CTTTATCCGA AATATGATAA TAAAGTAGAT
       CTCTTGCCAT TAACTACTGG CCTTGAATGG TGAACACTT TTATCTTAT AGAGGTAGAC CCCGTGGTGC GAAATAGGCT TTATATCATT ATTTCATCTA
```

```
+2301  AATCCAATCG AATAATTGTA AAAGTAATAA AAAATTAAGA ATAAAACCGC TTAACACACA CGAAAAAATA AGCTTGTTTT GCACTCTTCG TAAATTATTT
       TTAGGTTAGC TTATTAACAT TTTCATTATT TTTTAATTCT TATTTTGGCG AATTGTGTGT GCTTTTTTAT TCGAACAAAA CGTGAGAAGC ATTTAATAAA

+2401  TGTGAAGAAT GTAGAAACAG GCTTATTTTT TAATTTTTTT AGAAGAATTA ACAAATGTAA AAGAATATCT GACTGTTTAT CCATATAATA TAAGCATATC
       ACACTTCTTA CATCTTTGTC CGAATAAAAA ATTAAAAAAA TCTTCTTAAT TGTTTACATT TTCTTATAGA CTGACAAATA GGTATATTAT ATTCGTATAG

+2501  CCAAAGTTTA AGCCACCTAT AGTTTCTACT GCAAAACGTA TAATTTAGTT CCCACATATT AAGTAAACTT TGTCCTTAAC TCTCTCTGTC AGATTAGTTG
       GGTTTCAAAT TCGGTGGATA TCAAAGATGA CGTTTTGCAT ATTAAATCAA GGGTGTATAA TTCATTTGAA ACAGGAATTG AGAGAGACAG TCTAATCAAC

+2601  TAGGTGGCTT AAACTTAGTT TTACGAATTA AAAGGAGCCG GTGAAATGAA ATTTGTATCA TCATGGTAAT AGCTTTTCAG GCTCATTTCA
       ATCCACCGAA TTTGAATCAA AATGCTTAAT TTTCCTCGGC CACTTTACTT TAAACATAGT AGTACCATTA TCGAAAAGTC CGAGTAAAGT

+2701  CTATGACGGT AAAAGCAGAT TCTGTCGGGG AAGAAAAACT TCAAAATAAT ACACAAGCCA AAAAGACCCC TGCTGATTTA AAAGCTTTGC CAGATTCCTG
       GATACTGCCA TTTTCGTCTA AGACAGCCCC TTCTTTTTGA AGTTTTATTA TGTGTTCGGT TTTTCTGGGG ACGACTAAAT TTTCGAAACG GTCTAAGGAC
```

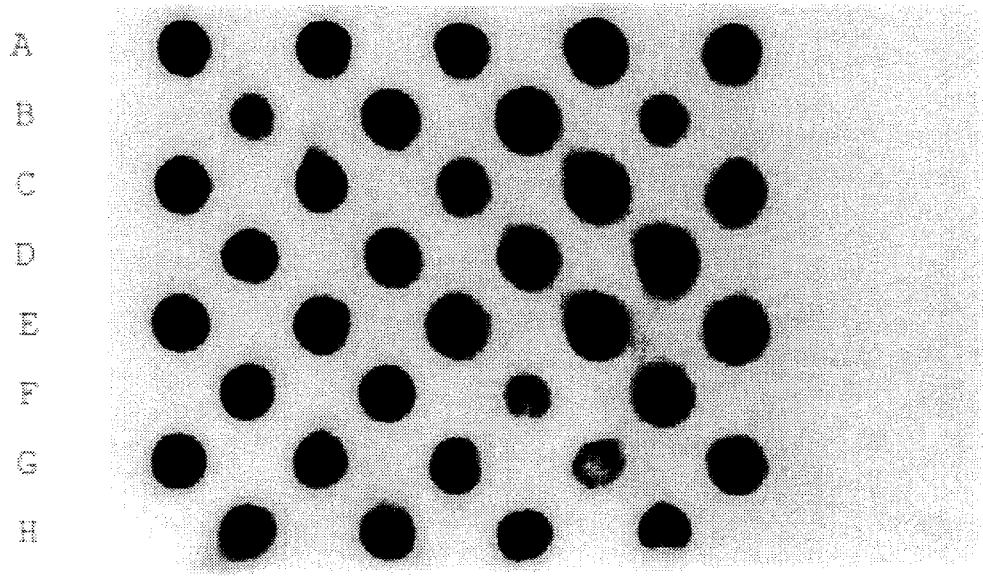
FIG. 4
 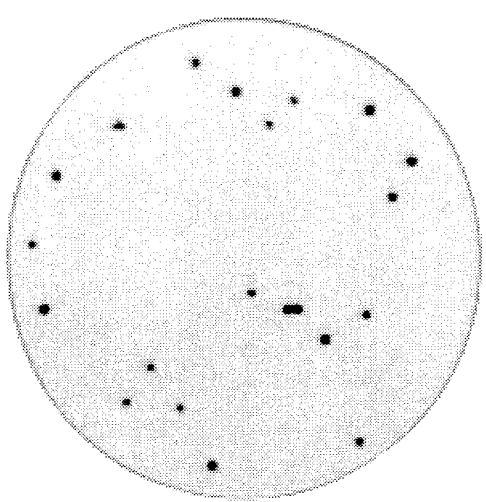
FIG. 5

DNA PROBES SPECIFIC FOR HEMOLYTIC LISTERIA

CROSS REFERENCES TO RELATED APPLICATIONS

This Application is a continuation of Application Ser. No. 07/829,277 filed Feb. 3, 1992, now abandoned which is a continuation-in-part of Application Ser. No. 07/227,402 filed Aug. 2, 1988, now abandoned, which is related to Application Ser. No. 07/143,490 filed Jan. 13, 1988, now abandoned. The entire disclosure of each of these applications is relied upon and incorporated herein by reference.

BACKGROUND OF THE INVENTION

*Listeria monocytogenes* is a facultative intracellular gram positive bacterium. The genus Listeria contains seven species: *L. monocytogenes, L. innocua, L. ivanovii, L. seeligeri, L. welshimeri, L. grayi,* and *L. murrayi*. Virulence of these species is quite diverse and *L. monocytogenes* is considered to be the only pathogenic species for humans. Pregnant women, new-born and immunocompromised patients are especially susceptible to infection. Another species of the genus, *L. ivanovii*, is also pathogenic but infections by this species are extremely rare and only affect animals.

*L. monocytogenes* is increasingly recognized as responsible for severe infections in both animals and humans. Although discovered in 1926, *L. monocytogenes* has only recently been recognized as a food pathogen after the tracing of epidemics to contaminated food (Kvenberg, 1988). Prolonged food conservation times and new eating habits have led to a real need for rapid detection of *L. monocytogenes*, which is able to grow in hostile conditions such as 4° C. and in up to 7% NaCl (Seeliger and Jones, 1986).

To avoid human infection, food sources have routinely been screened for the presence of Listeria organisms. Potential food sources infected with any species of Listeria have routinely been discarded to avoid infecting the consumer because of the time and expense involved in determining whether the infecting organisms are or are not pathogenic. Thus, there is a need for a means for identifying and readily and efficiently distinguishing between pathogenic and non-pathogenic Listeria species. This information is also necessary to determine the course of treatment of suspected Listeria infections and for the development of data for epidemiological studies.

SUMMARY OF THE INVENTION

The present inventors have fulfilled this need in the art by developing DNA probes capable of distinguishing pathogenic Listeria species from non-pathogenic Listeria species. It is demonstrated that a fragment internal to hlyA, the gene coding for listeriolysin O, specifically hybridizes to *L. monocytogenes* DNA under high stringency conditions. Two oligonucleotides were selected which are specific for *L. monocytogenes* among all species of the genus Listeria and among 59 bacterial species that can be found in food samples. These oligonucleotides are used for direct numeration of *L. monocytogenes* colonies grown on selective agar plates, after direct plating of contaminated food samples. In addition, the specificity of the oligonucleotides is used to develop a rapid method to detect *L. monocytogenes* in food samples using the PCR amplification technique.

This invention also relates to an oligonucleotide useful for detecting of hlyA gene of *Listeria monocytogenes*, wherein the oligonucleotide consists essentially of the sequence:

GAA TGT AAA CTT CGG CGC     (SEQ ID NO:1).

Another embodiment of this invention relates to another oligonucleotide useful for detecting of hlyA gene of *Listeria monocytogenes*, wherein the oligonucleotide consists essentially of the sequence:

CGA TGA TTT GAA CTT CAT C     (SEQ ID NO:2).

A further embodiment of this invention is another oligonucleotide useful for detecting of hlyA gene of *Listeria monocytogenes*, wherein the oligonucleotide consists essentially of the sequence:

GAA TGT AAA CTT CGG CGC AAT CAG     (SEQ ID NO:3).

Yet another embodiment of this invention is an oligonucleotide useful for detecting of hlyA gene of *Listeria monocytogenes*, wherein the nucleotide consists essentially of the sequence:

GCC GTC GAT GAT TTG AAC TTC ATC     (SEQ ID NO:4).

This invention also relates to a method of detecting *Listeria monocytogenes* in a sample to be tested comprising: providing a sample to be tested comprising DNA, wherein said DNA is accessible to a hybridization probe, contacting an oligonucleotide selected from the group consisting of:

1) GAA TGT AAA CTT CGG CGC (SEQ ID NO:1);
2) CGA TGA TTT GAA CTT CAT C (SEQ ID NO:2);
3) GAA TGT AAA CTT CGG CGC AAT CAG (SEQ ID NO:3); and
4) GCC GTC GAT GAT TTG AAC TTC ATC (SEQ ID NO:4);

with the sample, and detecting hybrid duplexes comprising said oligonucleotide and DNA of said sample.

This invention further provides a method of detecting *Listeria monocytogenes* in a sample to be tested comprising providing a sample comprising DNA to be tested, wherein the DNA of said sample is accessible to a hybridization probe, amplifying *L. monocytogenes* DNA present in the sample with oligonucleotide primers that specifically hybridize to the hlyA gene of *Listeria monocytogenes*, and detecting *L. monocytogenes* DNA amplified by polymerase chain reaction in the sample.

These and other embodiments of this invention are described more fully below.

BRIEF DESCRIPTION OF THE DRAWINGS

FIGS. 2-1, 2-2, and 2-3 depict the nucleotide sequence of the hlyA gene and its proximal region.

FIG. 3 depicts the schematic comparison of the amino acid sequences of listeriolysin O (LLO), streptolysin (SLO) and pneumolysin (PLY): sequences, represented by lines, are aligned on the unique cysteine (C) in the monologous position. Signal sequences are indicated by thick lines. The ( ) indicates deletions of one amino acid, and the numbers identify the coordinates in the protein sequence.

FIG. 4 depicts dot-colony hybridization of several Listeria species showing the specificity of oligonucleotide probes for *L. monocytogenes*.

FIG. 5 depicts the direct numeration of *Listeria monocytogenes* in naturally contaminated food.

DETAILED DESCRIPTION OF THE PREFERRED EMBODIMENTS

Figure 1:
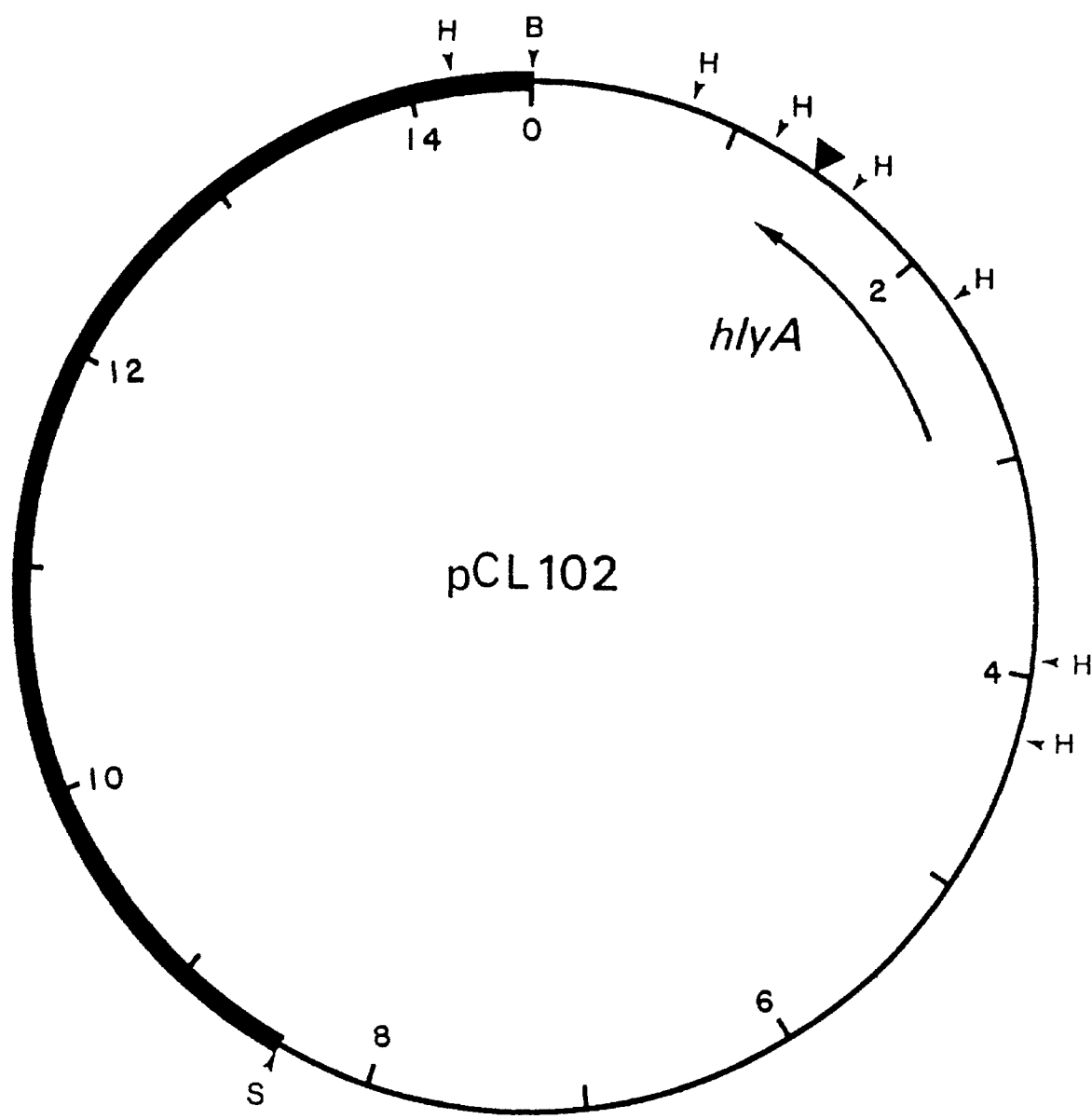
FIG. 1 is a restriction map of plasmid pCL102. The restriction site BamHI is indicated by "B"; SalI by "S"; and HindIII by "H". The inverted triangle corresponds to the insertion site of transposon Tn1545.
Figure 3:
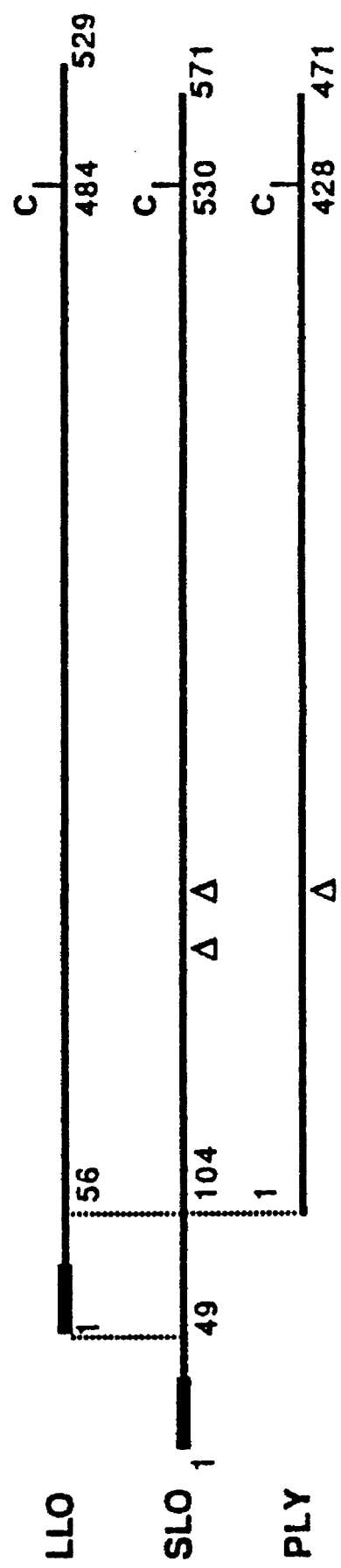

Among the virulence factors which enable Listeria organisms to enter, survive and grow within cells, including macrophages, the SH-activated hemolysin is a serious candidate. The first observation which suggested a correlation between hemolysin and virulence was that all non-hemolytic Listeria strains are experimentally non-pathogenic and that all pathogenic strains of Listeria produce zones of hemolysis on blood agar plates. Because hemolysin production is a phenotype easily identified on blood agar plates, genetic studies were undertaken and transposon mutagenesis was performed to obtain a non-hemolytic (Hly⁻) mutant.

The Hly⁻ mutant was avirulent; insertion of a single copy of the transposon had inactivated the hemolytic phenotype. Spontaneous loss of the transposon led to the recovery of the Hly⁺ phenotype and virulence. It was further shown that the Hly⁻ mutant, although phagocytosed at the same rate as that of the hemolytic revertant strain, stayed in the phagolysosome and failed to replicate significantly within the human enterocyte-like cell line Caco-2: electron microscopic study demonstrated that bacteria from the Hly⁻ mutant remained inside the phagosomes during cellular infection, whereas hemolytic bacteria from *L. monocytogenes* became free in the cytoplasm. These data were a strong indication that disruption of vacuole membranes by hemolysin-producing strains of *L. monocytogenes* might be a key mechanism allowing bacteria to escape from phagosome and to multiply within the cell cytoplasm.

The SH-activated hemolysin referred to herein as "Listeriolysin O" has been purified from *L. monocytogenes* culture supernatants. It shares the typical properties of other bacterial sulfhydryl-activated toxins: (i) inhibition with very low amounts of cholesterol, (ii) activation by reducing agents and suppression of the lytic activity by oxidation, and (iii) cross-reactivity with streptolysin O. Antiserum raised against the purified protein allowed the demonstration that the Hly⁻ mutant produced a truncated protein, indicating that the transposon had inserted in the listeriolyin O structural gene. Accordingly, the region of insertion of the transposon was cloned and sequence analysis showed that it had inserted in an open reading frame (ORF). The deduced sequence of this ORF shared homologies with streptolysin O and pneumolysin. From this, the identity of the locus of insertion of the transposon in the listeriolysin O gene, called hlyA, has been determined.

In order to elucidate the role of listeriolysin O in pathogenicity and to clarify the conflicting views on the nature and the number of Listeria hemolysin(s), a structural and functional analysis of the chromosomal region carrying hlyA was undertaken. In the examples which follow, the complete nucleotide sequence of hlyA and an extensive analysis of the deduced protein sequence, especially a comparison with other membrane-damaging thiol-activated hemolysins, is set forth. In addition, DNA-DNA hybridization studies, which indicate that the disclosed probes are present only in *L. monocytogenes*, are provided.

These analysis lead to the identification of the DNA sequence of a 2.8 kb portion of the *L. monocytogenes* genome. From this piece of chromosomal DNA, hlyA has been identified. Within this gene, a 651 bp HindIII fragment (oligo 1309–1965) is preferred for use as a probe. In addition, certain smaller oligos are contemplated for use as probes. Preferably, oligo 1775–1805 would make a suitable probe. In addition, oligos 1412–1441; 1643–1665; and 1810–1835 are contemplated for use as probes.

As one of ordinary skill in the art will note, the desired characteristics of these probes include their ability to hybridize with *L. monocytogenes* DNA while not hybridizing with DNA from other Listeria species. In addition, it is a preferred characteristic of these probes that they not cross-react with DNA from other hemolytic bacterial species, such as Streptococcus.

In addition to the probes discussed above, various improved probes are contemplated. In these probes, certain modifications are made which will not affect their ability to hybridize with the target DNA but will increase the strength of the hybridization bond and/or the ability of the hybridized probe to be detected. In part, these improvements include the replacement of certain base pairs with analogues or the modification of the probe to incorporate certain detection compounds.

In certain situations, it might be desired to replace some of the bases within the probe with non-base analogues. For example, the base adenine may be replaced with diaminopurine. This modification would result in a stronger bond between the probe and any homologous DNA present in a sample.

To facilitate detection of hybridized probe, various chemical modifications to the DNA sequence are possible. One example of these modifications includes sulfonating the DNA. Sulfonated DNA allows for increased detectability in reaction such as ELISA methods. In addition, through biotinylation, or the use of a biotin analog of a particular base, it is possible to incorporate a biotin site into the probe. The incorporation of a biotin site would facilitate detection of the hybridized probe in an avidinbiotin system.

Further, radiolabels can be incorporated into the probes for use and detection. At the present, $^{32}P$ is preferred for use as a label.

Various methods can be used with these probes to detect the presence of *L. monocytogenes* in a sample. These include radioimmunoassays (RIA); enzyme-linked immunosorbent essays (ELISA) and other types of diagnostic, qualitative essays commonly known to those of ordinary skill in the art.

EXAMPLE 1

Creation of pCL102

Identification of a DNA region encoding listeriolysin O:

Chromosomal DNA of hemolytic *L. monocytogenes* strain L028 digested with MboI had been cloned in the BamHI site of the cosmid vector pHC79. After transformation in *E. coli* HB101, several hemolytic clones were obtained, which were identified as ampicillin resistant colonies producing a halo of lysis on ampicillin blood agar plates. Spontaneous deletion of the original clones led to a stable derivative pCL101. Two deletions were created on the cosmid pCL101 between identical restriction sites (BamHI and Sal) to give pCL102, which contained an insert of 8.5 kilobases of *L. monocytogenes* DNA. Its restriction map is shown on FIG. 1.

The hemolytic activity detected in the extracts of *L. monocytogenes* strain HB101 as described by Boyer in J. Mol. Biol., 41:59–464 (1969), harboring pCL101 or pCL102 (7.5 HU/ml of overnight culture) is lower than that measured in the Listeria supernatants (64 HU/ml of overnight culture). By Western blot analysis of the extracts, using an antiserum against listeriolysin O, a protein of the same molecular weight as the listeriolysin O (60-kilodaltons) was detected.

Antilisteriolysin O serum preparation:

Female albino rabbits were immunized by repeated subcutaneous inoculations of highly purified hemolysin from *L. monocytogenes*. The protocol was based on 3 injections of 75 μg of toxin in complete Freund's adjuvant and one injection of the same dose in incomplete Freund's adjuvant. Blood was harvested 2 weeks after the last injection.

Western blot analysis:

For Western blot analysis, protein was electrophoretically transferred to nitrocellulose sheets in a Trans-Blot cell apparatus with blotting buffer containing 20% (v/v) methanol. The sheets were incubated for 1 h at room temperature with shaking in 50 mM Tris, 150 mM NaCl solution (pH 8.0) and 5% (w/v) skim milk prior to 1 h incubation in anti-listeriolysin O immune serum diluted (1:20) in the above buffer. The sheets were washed eight times in buffer before addition of 20 ml of milk buffer containing 1 mCi (0.37 kBq) of $^{125}$I-protein A. Shaking was continued for a further 1 h and then the filters were washed six times in buffer supplemented with 0.1% Triton X-100. The filters were dried at 80° C. and then autoradiographed using Kodak X-0-mat (SO-282) film.

EXAMPLE 2

Localization of hlyA in pCL102:

Localization of hlyA in pCL102 was achieved by using 400-base-pair DNA probe carrying part of the listeriolysin O gene called hlyA and part of Tn1545: a 410-base-pair HindIII fragment of pCL102 hybridized to the probe (FIG. 1). It revealed the presence of a stop codon, presumably the end of the hlyA gene.

Nucleotide sequence determination:

The dideoxy chain terminator sequencing method was used with the modification of Biggin et al. Proc. Nat'l. Acad. Sci. (USA) 80:3963–3965 (1983). The technique which generates sequential deletions of the insert starting at the cloning site using T4 polymerase was used as described by Dale et al., Plasmid 13:31–40 (1985).

Nucleotide sequence of hlFA:

The nucleotide sequence of hlyA and its upstream region is indicated on FIG. 2. The open reading frame, which ends in a 410 base-pair HindIII fragment (see below), starts in the 1670 base-pair HindIII fragment and is 1617 base-pairs long. The first ATG in the sequence is located 30 nucleotides downstream from the beginning of this ORF. It is preceded 10 nucleotides upstream by an hexanucleotide (AAGGAG) complementary to the 3' end of the 16 S RNA of *L. monocytogenes*. If this ATG is considered as the start codon of hlyA, the gene is 36% GC rich, a value which is in agreement with that calculated for *L. monocytogenes* (36–38%). This value is higher than that of the sequences adjacent to the gene.

The presence of a gram positive promoter-like sequence was investigated: upstream from the ORF, two TATAAT sequences were detected, but these sequences are not preceded by a "–35" sequence close to the consensus TTGACA. As hemolysin production is known to be regulated by factors, such as iron, the sequence was examined for sequences similar to the consensus identified as target for iron binding regulatory proteins, but none was detected. The exact location of the promoter can be determined.

Analysis of the deduced protein sequence:

The gene hlyA encodes a protein of 529 amino acids, which corresponds to a protein of 58.6 kDa. The amino-terminal sequence presents all the characteristics of signal sequences of gram positive bacteria: the first residues are hydrophilic and positively charged. They are followed by about twenty hydrophobic residues. The putative cleavage site of the signal peptidase lies probably after lysine 25 as the sequence starting at residue 26 is highly homologous to the amino-terminal sequence of the SH-dependent hemolysin secreted by *Listeria ivanovii*. The signal sequence of listeriolysin O has a length comparable to the average length of signal sequences of gram positive bacteria genes. Consequently, the secreted listeriolysin O (without the signal sequence) contains 504 amino acids and has a molecular mass of 55.8 kDa. This value is in agreement with the molecular weight of the protein purified from *L. monocytogenes* culture supernatants.

The amino acid composition of the protein does not reveal any special feature except the presence of a unique cysteine: this residue is located in the carboxy-terminal part of the sequence, in position 484. It is known that listeriolysin O, like all cytotoxins of the streptolysin O family, is thiol-activable. Reagents that block the SH-group inhibit the activity of this toxin, and in particular, inhibit binding to cholesterol which is thought to be the first step in the cytolytic activity of this protein. Thus, the carboxy-terminal region containing the unique cysteine is probably essential for activity. Two lines of evidence are in favor of this statement. (i) In the Hly-mutant, the transposon had inserted in codon 481 of hlyA, three codons upstream from the cysteine codon, giving rise to a truncated protein devoid of hemolytic activity. (ii) Comparison of listeriolysin O with two other SH-dependent hemolysins, streptolysins, streptolysin O and pneumolysin reveals the presence of a conserved undecapeptide containing the unique cysteine in the three proteins (see next Example).

EXAMPLE 3

Comparison of listeriolysin O with streptolysin O and pneumolysin:

It is well known that SH-activated hemolysins immunologically cross-react. It has been recently shown that streptolysin O from *Streptococcus pyogenes* and pneumolysin from *Streptococcus pneumoniae* share homologies. These proteins have identical molecular weight, if one takes into account the secreted form of streptolysin O, the pneumolysin being a non-secreted protein. When one aligns the sequences at the unique cysteine present in the carboxy-terminal end of these proteins, the highest homology lies in the region of this unique cysteine.

The amino acid sequence of listeriolysin O (LLO) was compared with the sequences of streptolysin O (SLO) and pneumolysin (PLY). These three proteins have similar sizes. The secreted forms of LLO and SLO are, respectively, 504 and 471 amino acids long, and pneumolysin is 471 amino acids long. The putative signal sequence of LLO (25 amino acids) is shorter than that of SLO (33 amino acids).

The three sequences can be completely aligned at the unique cysteine, if one introduces two deletions of one amino acid for SLO and one deletion of one amino acid for PLY. This alignment reveals strong homologies: the percentage of amino acid identity between two sequences compared two by two, in the common 469 residue region, is about 42–43%. Interestingly, the signal sequence of listeriolysin O corresponds to the N-terminal part of streptolysin O, the hydrophobic amino acids of listeriolysin O being changed for hydrophilic ones. This region is the region of lowest homology.

Homolgies between the three proteins are evident along the whole sequence but they are stronger towards the carboxy-terminal end. In particular, around the unique cysteine, an eleven amino acid peptide is conserved in the three sequences. If one compares the sequences in terms of similarity (and not identity), one observes even stronger homologics, illustrated by the superimposition of the hydrophobicity profiles.

At the DNA level, the genes do not show substantial homology (between 52% to 54% homologics when comparing any two of the three genes). Nevertheless, in the region coding for the conserved undecapeptide, the homology at the DNA level is 73% between ply and hlyA, 88% between slo and hlyA and 82% between slo and ply. These results are in agreement with previous results: when using a DNA fragment internal to slo as a probe, the homologics between *S. pyogenes* and *L. monocytogenes* could not be detected. Indeed, the probe used did not correspond to the region of highest homology and the conditions used could only detect 80% homology. It is highly probable that use of a probe corresponding to the nucleotide sequence coding for the common eleven amine acid region would have led to different results.

While listeriolysin O is homologous to toxins produced by Streptococci, Bacilli and Clostridii, the genes coding for these toxins do not, however, cross hybridize.

EXAMPLE 4

Detection of hlyA in the different species of the genus Listeria:

As listeriolysin O is now considered as a major virulence factor, it seemed interesting to test if hlyA was present in the different species of the genus Listeria. By Southern blot analysis, the presence of hlyA in several *L. monocytogenes* strains and in the other species of the genus, i.e., *L. ivanovii, L. seeligeri, L. innocua, L. welshimeri,* and *L. murrayi,* was investigated. As a probe, a DNA fragment internal to the gene was used: the 651-base-pair HindIII fragment which extends from codon to codon. The results, with the probe used, were unambiguous. The gene hlyA is only detected in *L. monocytogenes,* even in the strains which are non-hemolytic, such as the strain ATCC 15313 and Audurier 86/776.

Detection of hlyA by Polymerase Chain Reaction:

Polymerase Chain Reaction (PCR) is a method of specifically amplifying DNA sequences present in low concentration within a test sample. By way of example, this method involves two oligonucleotide primers complementary to the ends of a DNA sequence sought to be amplified. Through a series of denaturation, primer annealing, and elongation steps the desired sequence is amplified. While absolute sequence complementarity between the primer and the target sequence is not required, the denaturation temperature of the oligonucleotide primer-target DNA hybrid is ordinarily between 47° C. and 65° C.

The annealing temperature can be determined experimentally. Alternatively, it can be calculated from the base composition and degree of complementarity of the probe to the target DNA. The determination of annealing temperature from DNA sequence information accounting for mismatch is based on the following equation:

$$TD=4(G+C)+2(A+T)-5 \qquad \text{(Wallace's Rule)}$$

In preferred embodiments of this invention, the length of the oligonucleotide primer is generally between 18 bases and 26 bases, with the length of the primer optimally about 24 bases. The primer can be chemically synthesized using well known methods. The oligonucleotides are hybridized to the target DNA and function as primers for a thermostable DNA polymerase, such as Taq polymerase isolated from *Thermus aquaticus*. Taq polymerase is commercially available from Cetus Perkin Elmer, Norwalk, Conn. Other suitable DNA polymerases include TUB DNA polymerase available from Amersham Corp., Arlington Heights, Ill., or VENT DNA polymerase which is available from New England Biolabs.

Through repeated cycles of heating and cooling to denature, specifically anneal primers to the target DNA, and enzymatically synthesize DNA from the hybridized primer using a thermostable DNA polymerase, the target DNA which may represent a small fraction of the DNA in the sample is specifically amplified. This method can be used, for example, as a sensitive assay for specific DNA sequences within a sample. If the desired sequence is present, the PCR technique will amplify it to a level where it can be detected. If no sequence complementary to the primers exists, no DNA will be amplified by PCR.

By way of example, PCR amplification can be performed using a Techne PHC2 apparatus or other equivalent devices. The reaction mixture can contain 1× Cetus PCR buffer (500 mM KCl, 100 mM Tris-HCl, pH 8.3, 15 mM $MgCl_2$, 0.1% gelatin sterilized by filtration, 200 μM of each of the deoxynucleoside triphosphates, 300 ng of each primer, 10 μl of DNA preparation containing the sequence to be amplified, and 1 unit of Taq DNA polymerase in a total volume of 100 μl.

The template DNA is initially denatured at 94° C. for 5 minutes, and then cycles of PCR amplification are run. In specific embodiments of this invention, cycles of PCR amplification can be run under the following conditions: denaturation at 94° C. for 1 min., primer annealing at 65° C. for 1 min, and DNA extension at 70° C. for 2 min. Typically about 30 cycles of amplification are performed.

The sequence and/or size of the amplified DNA can be determined as part of a sensitive assay for the presence of the target sequence within a sample. By way of example, the amplified DNA can be analyzed by agarose gel electrophoresis, restriction digest analysis, or hybridization to a specific probe.

Several primers were tested and were found to be useful for the detection of hlyA of *L. monocytogenes* using PCR amplification. Criteria used in selecting these primers include length and low sequence homology to the genes encoding streptolysin O and pneumolysin. Two primers that were found to be highly specific for *L. monocytogenes* DNA are PCRA and PCRB. Primer PCRA, extending from nucleotide 1421 to nucleotide 1438 of the hlyA gene as depicted in FIG. 2, has the sequence:

GAA TGT AAA CTT CGG CGC            (SEQ ID NO:1)

Primer PCRB, extending from nucleotide 1803 to nucleotide 1785 of the hlyA gene depicted in FIG. 2, has the sequence:

CGA TGA TTT GAA CTT CATC        (SEQ ID NO:2).

Two other nucleotide primers that were very specific for the detection of *L. monocytogenes* hlyA by PCR were PCRGO and PCRDO. PCRGO, corresponding to nucleotides 1421 to nucleotide 1444 of the hlyA gene as depicted in FIG. 2, has the sequence:

GAA TGT AAA CTT CGG CGC AAT CAG       (SEQ ID NO:3).

Nucleotide PCRDO, extending from nucleotides 1808 to 1785 of the hlyA gene as depicted in FIG. 2, has the sequence:

GCC GTC GAT GAT TTG AAC TTC ATC       (SEQ ID NO:4).

As shown in Table I, these primers specifically hybridized only with the DNA of *L. monocytogenes*, and not with the DNA of other closely related species of microorganisms in colony hybridization experiments.

TABLE 1

Specificity of oligonucleotides for Listeria and other species:

| Strains | | Reference or Number Characteristics | Reactivity with Labeled PCRA or PCRB |
|---|---|---|---|
| Type strains of Listeria species: | | | |
| L. monocytogenes | 1/2 a | CLIP 12498 | + |
| L. monocytogenes | 1/2 b | CLIP 12499 | + |
| L. monocytogenes | 1/2 c | CLIP 12500 | + |
| L. monocytogenes | 3 a | CLIP 12501 | + |
| L. monocytogenes | 3 b | CLIP 12502 | + |
| L. monocytogenes | 3 c | CLIP 12503 | + |
| L. monocytogenes | 4 a | CLIP 12504 | + |
| L. monocytogenes | 4 b | CLIP 12505 | + |
| L. monocytogenes | 4 c | CLIP 12506 | + |
| L. monocytogenes | 4 d | CLIP 12507 | + |
| L. monocytogenes | 4 e | CLIP 12508 | + |
| L. monocytogenes | 7 | CLIP 12509 | + |
| L. monocytogenes | type 1 | V 7 | + |
| L. monocytogenes | 4 b | Scott A | + |
| L. innocua | 6 a | ATCC 33090 | − |
| L. innocua | 6 b | CLIP 12512 | − |
| L. ivanovii | 5 | ATCC 19119 | − |
| L. ivanovii | 5 | CLIP 2300 | − |
| L. ivanovii | 5 | CLIP 2737 | − |
| L. ivanoviii | 5 | CLIP 12065 | − |
| L. seeligeri | 1/2 b | ATCC 35967 | − |
| L. welshimeri | 6 b | ATCC 35897 | − |
| L. murrayi | — | ATCC 25401 | − |
| L. grayi | — | ATCC 19210 | − |
| Closely related species: | | | |
| Brochorix thermosphacta | | AC 11509 | − |
| Brochorix thermosphacta | | | − |
| Kurthia | | | − |
| Kurthia | | | − |
| Rhodococcus equi | | | − |
| Staphylococcus aureus | | beta-hemolytic | − |
| Bacillus cereus | | | − |
| Streptococcus faecium | | | − |
| Staphylococcus hominis | | ATCC 27844$^T$ | − |
| Staphylococcus warneri | | ATCC 12836$^T$ | − |
| Staphylococcus haemolyticus | | ATCC 29970$^T$ | − |
| Staphylococcus simulans | | ATCC 29848$^T$ | − |
| Staphylococcus sciuri | | ATCC 29062$^T$ | − |
| Staphylococcus epidermidis | | ATCC 14990$^T$ | − |
| Staphylococcus caseolyticus | | ATCC 13548$^T$ | − |
| Staphylococcus aureus III | | ATCC 12600$^T$ | − |
| Staphylococcus hyicus | | ATCC 11249$^T$ | − |
| Staphylococcus chromogenes | | ATCC 10530$^T$ | − |
| Staphylococcus xylosus | | ATCC 29971$^T$ | − |
| Strains isolated from children and adults: | | | |
| L. monocytogenes | 1/2 a | 6 | + |
| L. monocytogenes | 1/2 b | 6 | + |
| L. monocytogenes | 4 b | 8 | + |
| Listeria sp. isolated from food products: | | | |
| L. monocytogenes | 1/2 a | 19 | + |
| L. monocytogenes | 1/2 b | 11 | + |
| L. monocytogenes | 1/2 c | 9 | + |
| L. monocytogenes | 3 b | 2 | + |
| L. monocytogenes | 4 b | 19 | + |
| L. monocytogenes | 3 c | 1 | + |
| L. innocua | 6 a | 8 | − |
| L. innocua | 6 b | 9 | − |
| L. innocua | nd | 52 | − |
| L. seeligeri | 1/2 b | 3 | − |
| L. seeligeri | 6 b | 3 | − |
| L. seeligeri | nd | 2 | − |
| L. welshimeri | nd | 6 | − |
| Strains isolated from selective medium for Listeria | | | |
| Enterococcus sp. | | 19 | − |
| Micrococcus sp. | | 12 | − |
| Pseudomanas sp. | | 9 | − |

T, Type strain
ATCC, American Type Culture Collection, Rockville, Md.
CLIP, Collection Listeria Institut Pasteur

EXAMPLE 5

Numeration and Rapid Detection by PCR of *L. monocytogenes*

Materials and Methods:
Bacterial strains and culture media:
The bacterial strains used to test the specificity of the oligonucleotide probes are listed in Table I. They include 26 Listeria strains (type strains and strains used as reference for serovar determination), 19 closely related species, 20 clinical *L. monocytogenes* strains isolated in France in 1990 from adult and children patients, 144 Listeria strains isolated from food including dairy and meat products and 40 strains isolated on selective agar media during classical procedures for *L. monocytogenes* detection in food.

These results indicate that PCRA and PCRB specifically hybridize only to *Listeria monocytogenes* and not with other closely related species.

All bacterial strains were routinely grown overnight at 37° C in Brain Heart Infusion (BHI) or in trypticase soy broth (TSY) supplemented with 0.6% yeast extract (BBL Microbiology Systems, Cockeysville, Md.). The selective media used were Oxford agar base and supplements (Oxoid), PALCAM base (Merck) and MOX (Oxoid) (McClain and Lee, 1988). Enrichment broth (EB) and Modified Enrichment Broth (MEB) used before detection by PCR were as described (Lovett, 1987) (Klinger and Johnson, 1988) except that acriflavin was used at concentration of 10 mg/ml.
Oligonucleotides:
Oligonucleotides were synthesized in a Cyclone DNA synthesizer (Biosearch, Inc., USA) and used without further purification.

PCRA=GAATGTAAACTTCGGCGC (SEQ ID NO:1) (positions 747 to 764 of the hlyA gene). PCRB= CGATGATTTGAACTTCAT (SEQ ID NO:2) (complementary to positions 1111 to 1129 (of the hlyA gene).
PCRGO=GAATGTAAACTTCGGCGCAATCAG (SEQ ID NO:3) (positions 747 to 770 of the hlyA gene).
PCRDO=GCCGTCGATGATTTGAACTTCATC (SEQ ID NO:4) (complementary to positions 1111 to 1134 of the hlyA gene).

Labeling was performed with ATP-gamma $^{32}$P and the T4 polynucleotide kinase as previously described (Maniatis et al., 1982).

Preparation of food samples for direct numeration.

Samples included dairy products or meat products and were generally used without further cooking. 25 g or 10 g food-aliquots were suspended in 225 ml or 90 ml, respectively, of TSY and if necessary homogenized for 2 min in a homogenizer. The homogenate (0.1 ml or 1 ml of 1:10 dilution) was plated onto Oxford, PALCAM or MOX on 100 mm and 140 mm plates. When necessary, Listeria-free food samples (e.g., raw milk, cheese, sausage, fish-eggs) were artificially contaminated by appropriate dilutions of overnight cultures of L. monocytogenes or L. innocua and plated on selective media.

Filter preparation and hybridization conditions.

To test the specificity of the oligonucleotides, 2.5 μl of each overnight culture were spotted in a regular array onto agar plates and incubated overnight at about 30° C. Colonies were then transferred to Whatman n°451 filter paper filters. Colony prints were then lysed by alkali and microwaved as described by Datta (Datta, 1987). Filters were stored up to several weeks at room temperature. Triplicate filters were hybridized under high stringency conditions using labeled PCRA or PCRB or an equimolar mixture of PCRA and PCRB as probes.

Filters were soaked in a 6× SSC, Denhardt 5× buffer at room temperature for 15 minutes, and then were hybridized overnight at 40° C. in hybridization buffer (6× SSC, 5× Denhardt, 1 mM EDTA, 100 μg/ml denatured calf thymus DNA) and either labeled PCRA or PCRB or an equimolar mixture of labeled PCRA and PCRB was added to give a final concentration of $10^6$ cpm per ml.

The filters were then washed in 5× SSC, first at room temperature for a few minutes, and then twice more at 50° C. for one hour. Filters were finally washed for 5 to 10 minutes in 2× SSC at 50° C, air dried and autoradiographed with an intensifying screen for several hours.

The same procedure was used to transfer the colonies grown from food samples, except that the plates were photographed before transfer and the number of characteristic colonies determined.

Direct enumeration by colony hybridization

The procedure was similar to that used to test the specificity of the oligonucleotides: the colonies which grew from food samples on selective media plates were transferred onto filters which were then hybridized and autoradiographed. Before transfer, the plates were photographed and the number of colonies surrounded by the esculin-positive black halo was counted. The black spots on the filters were also counted.

PCR amplification.

25 g food-aliquots were suspended in 225 ml of EB and if necessary homogenized for 2 min in a homogenizer. The suspension was then incubated 24 h at 30° C. under slow agitation and 1 ml was used to inoculate 30 ml of MEB. This second enrichment culture was performed 24 h at 30° C. under slow agitation.

Bacterial cells from 1 ml of enrichment culture or 0.5 ml of overnight pure Listeria culture were pelleted, resuspended in 60 μl of lysis buffer (0.01M Tris pH 8.3; 20% sucrose; 41.5 mg/ml lysozyme) and incubated 1 h at 37° C. Then 200 μl of TE (10 mM Tris HCl pH 7.5; 1 mM EDTA) and 3 μl of a 20 mg/ml proteinase K solution were added before a 1 h incubation at 55° C. followed by a 30 min incubation at 90° C. Tubes were then centrifuged 2 min at 12000 rpm and 10 μl of supernatant was used for PCR amplification.

PCR amplification was performed by using a Techne PHC2 apparatus (Techne). The reaction mixture contained 1× PCR buffer (Cetus), 200 μM of each of the deoxynucleoside triphosphates, 300 ng of each of the primers (PCRGO and PCRDO), 10 μl of the DNA preparation, and 1 U of Taq DNA polymerase (Perkin-Elmer Cetus Corp., Norwalk, Conn.) in a total volume of 100 μl. Template DNA was initially denatured at 94° C. for 5 min, and then 30 cycles of PCR amplification were run under the following conditions: denaturation at 94° C. for 1 min, primer annealing at 65° C. for 1 min, and DNA extension at 70° C. for 2 min. Amplified products were detected by electrophoresis of 20 μl of the reaction mixture in a 1.4% agarose gel (containing 1% ethidium bromide) in Tris-borate-EDTA buffer. Specificity of the amplification was tested by digestion of 80 μl of the reaction mixture with 7.5 U of RsaI in a final volume of 100 μl and analysis by agarose electrophoresis after ethanol precipitation.

Results:

1. Synthetic Oligonucleotides as Specific Probes for L. monocytogenes

Two oligonucleotides, PCRA and PCRB, were chosen in the 651 base pair fragment of hlyA within the region of lowest similarity between hlyA and the genes coding for streptolysin O and pneumolysin. The specificity of each of these oligonucleotides was tested by colony hybridization under high stringency conditions, using PCRA alone, PCRB alone or an equimolar mixture of PCRA and PCRB. Positive signals were only obtained with L. monocytogenes strains in the genus Listeria. See Table 1. As opposed to signals of various intensities obtained when a single oligonucleotide was used, use of the mixture of the two resulted in signals of identical intensity. None of the other bacterial strains tested, including those frequently isolated from food, scored positive with either of the two oligonucleotides.

The specificity of PCRA and PCRB L. monocytogenes is depicted in FIG. 4. Dot-colony hybridization of a mixture of PCRA and PCRB oligonucleotides to the following colonies are shown:

Listeria isolated from children and adults:

L. monocytogenes (serovar* 1/2a): A1, C1, E1, G1, B2 and D2;

L. monocytogenes (serovar 1/2b): F2, H2, A3, C3, E3 and G3;

L. monocytogenes (serovar 4b): B4, D4, F4, H4, A5, C5, E5 and G5;

Listeria from dairy and meat products:

L. monocytogenes (serovar 1/2a): B6, D6 and F6;

L. monocytogenes (serovar 1/2b): H6, A7 and C7;

L. monocytogenes (serovar 3b): E7 and G7;

L. monocytogenes (serovar 1/2c): B8, D8 and F8;

L. monocytogenes (serovar 3c): H8;

L. monocytogenes (serovar 4b): A9; C9; E9 and G9;

L. innocua: B10; D10; F10 and H10;

L. seeligeri: A11; C11; E11 and G11;

L. welshimeri: B12; D12; F12 and H12.

*A serovar, or serotype, is a group of strains that exhibits distinctive antigenic properties.

The same analysis was performed with 59 other bacterial strains frequently isolated from food shown in Table 1. None of them reacted with the probes. See Table 1.

2. Use of Oligonucleotides for Direct Numeration in Artificially and Naturally Contaminated Food In order to evaluate the degree of *L. monocytogenes* contamination of food samples, a direct numeration method was established. Previously, the technique of numeration of *L. monocytogenes* present in food samples was time consuming relying on the direct plating of serial dilutions of samples on selective agar plates, such as Oxford, PALCAM and MOX. On these selective media, all Listeria grow as well as some Staphylococci and Streptococci. Colonies that are viable are then analyzed and identified as *L. monocytogenes* on the basis of their biochemical characteristics. This last step of biochemical identification has been replaced here by colony hybridization using the mixture PCRA+PCRB as a probe.

To test the efficiency of the technique whatever the food sample origin, various food samples were artificially contaminated with *L. monocytogenes* alone or in association with *L. innocua*. All *L. monocytogenes* detected by the classical technique were detected with the oligonucleotides. None of the *L. innocua* reacted with the probes. As shown in FIG. 5 and Table II, the technique was equally successful with naturally contaminated samples. No false positive signals were observed.

In FIG. 5, an Oxford agar plate is depicted on the left, showing the presence of many bacteria. In the Oxford agar plate, all Listeria species exhibit a halo around the colonies. On the right, an autoradiograph of the same plate is depicted after colony hybridization using a mixture of PCRA and PCRB as a probe. Only *L. monocytogenes* colonies react with the probe. As shown in FIG. 5, the technique can also be applied to naturally contaminated samples.

TABLE 2

Direct numeration of *L. monocytogenes* in naturally contaminated food samples

| Food sample | Nb of typical esculin positive Listeria colonies per plate | Nb of colonies identified by classical biochemical test per plate | Nb of "spots" on the autoradiogram |
|---|---|---|---|
| sausage | 4 | 2 | 2 |
| sausage | 3 | 1 | 1 |
| sausage | 11 | 4 | 4 |
| sausage | 4 | 2 | 2 |
| small sausage | 10 | 0 | 0 |
| small sausage | 10 | 0 | 0 |
| small sausage | 3 | 0 | 0 |
| small sausage | 1 | 0 | 0 |
| sausage meat | 1 | 0 | 0 |
| sausage meat | 4 | 0 | 0 |
| sausage meat | 1 | 0 | 0 |
| sausage meat | 0 | 0 | 0 |
| sausage meat | 1 | 0 | 0 |
| sausage meat | 1 | 1 | 1 |
| sausage meat | 0 | 0 | 0 |
| sausage meat | 1 | 0 | 0 |
| cheese | 26 | 26 | 24 |
| dry hard sausage | 13 | 0 | 0 |
| dry hard sausage | 14 | 0 | 0 |
| rillettes | 81 | 0 | 0 |
| rillettes | 13 | 1 | 1 |

3. Detection of *L. monocytogenes* in Food Samples by PCR

In order to reduce the time necessary for the specific detection of *L. monocytogenes* in foodstuff, two other oligonucleotides were used (PCRGO, PCRDO). PCRGO and PCRDO, which are slightly longer than PCRA and PCRB, were assayed for specificity as primers on pure chromosomal DNA. The specificity of the amplification was evaluated by the presence or absence of a 388 bp fragment and was confirmed by digestion with RsaI, a restriction enzyme which cuts the amplified fragment only once resulting in two fragments that can be detected easily on agarose gels.

Figure 6:
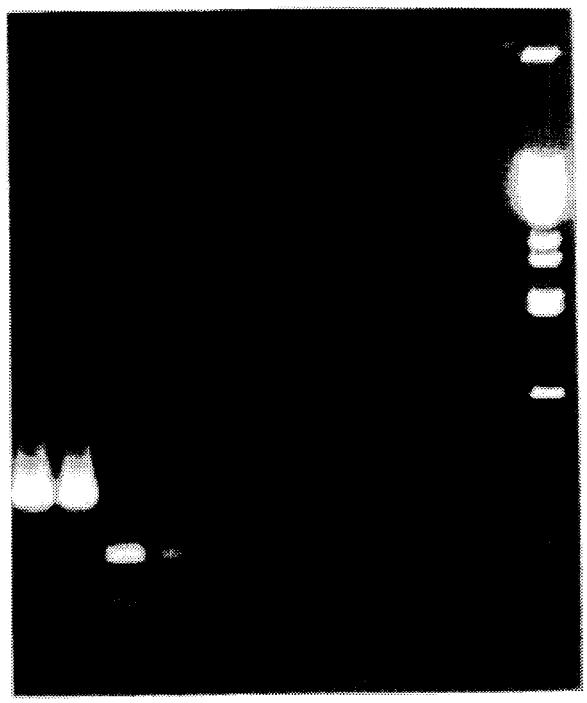
FIG. 6 depicts the PCR amplification of chromosomal DNA of different Listeria species using oligonucleotide primers specific for *L. monocytogenes*.

In FIG. 6, PCR amplified chromosomal DNA of different Listeria species with the PCRDO and PCRGO primers were analyzed by gel electrophoresis:

Lanes 1 and 3: *L. monocytogenes* strain EGD (serovar 1/2b);

Lanes 2 and 4: *L. monocytogenes* strain LO28 (serovar 1/2c);

In lanes 3 and 4, the PCR products were cleaved by RsaI before electrophoresis;

Lane 5: *L. seeligeri* (type strain);

Lane 6: *L. seeligeri*

Lane 7: *L. ivanovii* ( type strain );

Lane 8: *L. ivanovii* ;

Lane 9: *L. innocua* ( type strain );

Lane 10: *L. welshimeri* (type strain);

Lane 11: *L. murrayi* (type strain);

Lane 12: *Lambda DNA* cut with BstEI (standard).

As shown in FIG. 6, only *L. monocytogenes* DNA was amplified, and the detected fragment cleaved in two fragments by RsaI. In addition, all strains of *L. monocytogenes* from all serovars were positive in this test (FIG. 7).

Figure 7:
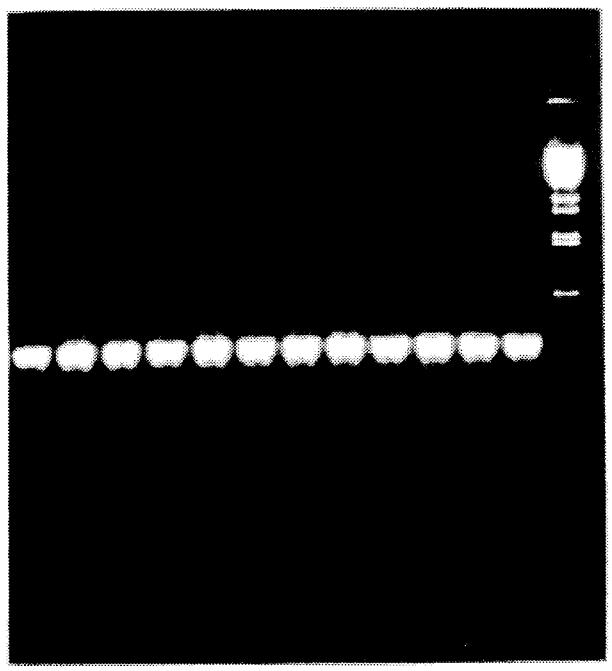
FIG. 7 depicts the PCR amplification of DNA of *L. monocytogenes* of different serovars.

In FIG. 7, PCR amplified chromosomal DNA of different *L. monocytogenes* serovars using PCRDO and PCRGO primers were analyzed by gel electrophoresis:

Lane 1: serovar 1/2a;

Lane 2: serovar 1/2b;

Lane 3: serovar 1/2c;

Lane 4: serovar 3a;

Lane 5: serovar 3b;

Lane 6: serovar 4d;

Lane 7: serovar 3c;

Lane 8: serovar 4e;

Lane 9: serovar 4b;

Lane 10: serovar 4c;

Lane 11: serovar 7;

Lane 12: serovar 4a;

Lane 13: lambda DNA cut with BstEI (standard).

The specific detection of *L. monocytogenes* in food samples by direct amplification was performed after a 48 hour enrichment period and analysis of a 1 ml sample as described supra. In a double-blind study performed on 180 food samples of various origins (miilk, meat, ice cream, sausage, chicken), all *L. monocytogenes* contaminated samples were detected by the PCR technique. Moreover, some samples that had been found positive by PCR after two days of enrichment, were first found negative. By the classical technique, a positive result was only obtained after a seven day enrichment period.

The sensitivity of the technique was tested with artificially contaminated samples. Presence of ten bacilli in 25 g of food before enrichment was always detected within two days by PCR technique. Inoculation of 100 bacilli per ml of enrichment broth always led to a positive result.

In summary, the discovery that hlyA, the gene coding for listeriolysin O, an important virulence factor, was only detected in the pathogenic species *L. monocytogenes* by hybridization under high stringency conditions, has led to the use of synthetic oligonucleotides derived from hlyA for the direct numeration of *L. monocytogenes* in food samples by colony hybridization, after growth on selective media. This technique avoids the time consuming classical techniques and allows treatment of large numbers of filters in the same time, a serious advantage when large numbers of food samples are to be tested during epidemic surveys.

In the food industry, rapid detection of *L. monocytogenes* is increasingly required by industry and consumers. The detection system of this invention makes use of the now standard PCR amplification technique. This invention has been validated by a blind study of contaminated food samples tested by the FDA approved classical technique as well as the PCR technique and has proven useful for surveying dairy products for more than one year. The enrichment period is necessary to avoid false negatives. The method of the instant invention is highly specific, and up to now, false positives have not been obtained. This invention is applicable to a variety of food compositions, and is believed to be the first use of a specific probe in a PCR amplification assay of food samples. This technique readily discriminates *L. monocytogenes* from *L. innocua*, a non-pathogenic species of Listeria often present in foodstuffs, in contrast to the commercially available immunoenzymatic or hybridization kits, which often do not distinguish these species.

The sensitivity of this technique ($10^2$ bacteria per ml) is equivalent to the sophisticated technique based on immunomagnetic separation (Skerge et al., 1990) and is considerably higher than those of the commercialized immuno detection techniques (Kerr et al., 1990; Mattingly et al., 1988; Klinger et al., 1988; King et al., 1989) which have detection limits of about $10^5$ bacteria per ml.

REFERENCES CITED

Dalta, A. R., Wentz, B. A. and Hill, W. E., (1987), Detection of hemolytic *Listeria monocytogenes* by using DNA colony hybridization. Appl. Environ. Microbiol. 53: 2256–2259.

Kerr, K. G., Rostova, N. A., Hawkey, P. M. and Lacey, R. W. Incidence of Listeria sp. in precoded, chilled chicken products as determined by culture and enzyme-linked immunoassay (ELISA) J. Food Prot., 53:606–607.

King, W., Raposa, S., Warshaw, J., Johnson, A., Halbert, D. and Klinger, J. D. (1989), A new colorimetric nucleic acid hybridization assay for Listeria in foods. Int. J. Food Microbiol., 8:225–232.

Klinger, J. D. (1988), Isolation of Listeria: a reviw of procedures and future prospects. Infection, 16:98–105.

Klinger, J. D. and Johnson, A. R., (1988), A rapid nucleic hybridization assay for Listeria in foods. Food Technol. 42: 66–70.

Kvenberg, J. E., (1988), Outbreaks of listeriosis/Listeria-contaminated foods. Microbiol. Sciences 5: 355–358.

Lovett, J., (1987), Listeria isolation. Anal. Chem. Suppl. to 6th Edition, Assoc. Anal. Chem., Arlington, Va.

Maniatis, T., Fritsch, E. F. and Sambrook, J., (1982), Molecular Cloning, a laboratory manual.

Mattingly, J. A., Butman, B. T., Plank, M. C. and Durham, R. J. (1988), Rapid monoclonal-based enzyme-linked immunosorbent assay for detection of Listeria in foods. J. Assoc. Off. Anal. Chem., 71:679–681.

Seeliger, H.P.R. and Jones, D., (1986) Genus Listeria Pirie 1940, 383 $^{AL}$. In: Berger's Manual of Systematic Bacteriology. Sneath, P.H.A., Mair, N. S., Sharpe, N. E. and Holt, J. G. (eds). The Williams and Wilkins Co., Baltimore, Md., pp 1235.

Skjerve, E., Rorvik, L. M. and O. Olsvik (1990), Detection of *Listeria monocytogenes* in foods by immunomagnetic separation. appl. Environ. Microbiol., 56:3478–3481.

---

What is claimed is:

1. An oligonucleotide useful for the detection of hlyA gene of *Listeria monocytogenes*, wherein the oligonucleotide has the sequence:

GAA TGT AAA CTT CGG CGC        (SEQ ID NO:1).

2. An oligonucleotide useful for the detection of hlyA gene of *Listeria monocytogenes*, wherein the oligonucleotide has the sequence:

CGA TGA TTT GAA CTT CAT C        (SEQ ID NO:2).

3. An oligonucleotide useful for the detection of hlyA gene of *Listeria monocytogenes*, wherein the oligonucleotide has the sequence:

GAA TGT AAA CTT CGG CGC AAT CAG    (SEQ ID NO:3).

4. An oligonucleotide useful for the detection of hlyA gene of *Listeria monocytogenes*, wherein the oligonucleotide has the sequence:

GCC GTC GAT GAT TTG AAC TTC ATC    (SEQ ID NO:4).

5. A method of detecting *Listeria monocytogenes* in a sample to be tested, comprising:

a) providing a sample to be tested comprising DNA, wherein the DNA of said sample is accessible to a hybridization probe; and b) contacting an oligonucleotide selected from the group consisting of:

1) GAA TGT AAA CTT CGG CGC (SEQ ID NO:1);

2) CGA TGA TTT GAA CTT CAT C (SEQ ID NO:2);

3) GAA TGT AAA CTT CGG CGC AAT CAG (SEQ ID NO:3); and

4) GCC GTC GAT GAT TTGAAC TTC ATC (SEQ ID NO:4);

to the DNA of said sample under high stringency hybridization conditions; and c) detecting hybrid duplexes comprising said oligonucleotide and DNA of said sample.

6. The method of detecting *Listeria monocytogenes* as claimed in claim 5, wherein said DNA of the sample to be tested is immobilized on filters.

7. A method of detecting *Listeria monocytogenes* in a sample to be tested, comprising:

a) providing a sample to be tested comprising DNA, wherein the DNA of said sample is accessible to a hybridization probe;

b) amplifying *L. monocytogenes* DNA present in the sample using polymerase chain reaction with oligonucleotide primers that specifically hybridize to the hlyA gene of *Listeria monocytogenes*, wherein said oligonucleotide primers are GAA TGT AAA CTT CGG CGC (SEQ ID NO:1); and CGA TGA TTT GAA CTT CAT C (SEQ ID NO:2); and c) detecting *L. monocytogenes* DNA amplified by polymerase chain reaction in the sample.

8. A method of detecting *Listeria monocytogenes* in a sample to be tested, comprising:

a) providing a sample to be tested comprising DNA, wherein the DNA of said sample is accessible to a hybridization probe;

b) amplifying *L. monocytogenes* DNA present in the sample using polymerase chain reaction with oligonucleotide primers that specifically hybridize to the hlyA gene of *Listeria monocytogenes*, wherein said oligonucleotide primers are GAA TGT AAA CTT CGG CGC AAT CAG (SEQ ID NO:3); and GCC GTC GAT GAT TTG AAC TTC ATC (SEQ ID NO:4); and c) detecting *L. monocytogenes* DNA amplified by polymerase chain reaction in the sample.

9. The method of detecting *Listeria monocytogenes* as claimed in claim 7 or 8, wherein said polymerase chain reaction comprises about 30 cycles of:

a) denaturation at about 94° C. for about 1 min.;

b) primer annealing at about 65° C. for about 1 min.; and c) DNA extension at about 70° C. for about 2 min.

10. The method of detecting *Listeria monocytogenes* as claimed in claim 9, wherein said DNA extension is catalyzed by a thermostable DNA polymerase selected from the group consisting of Taq, TUB, and VENT.

11. The method of detecting *Listeria monocytogenes* as claimed in claim 10, wherein the detecting of *L. monocytogenes* DNA amplified by polymerase chain reaction is performed by gel electrophoresis.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GAATGTAAAC TTCGGCGC 18

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CGATGATTTG AACTTCATC 19

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GAATGTAAAC TTCGGCGCAA TCAG                                                                       24

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCCGTCGATG ATTTGAACTT CATC                                                                       24